(12) United States Patent
Mitsuhashi et al.

(10) Patent No.: US 7,214,781 B2
(45) Date of Patent: May 8, 2007

(54) GENE MARKERS FOR LUNG CANCER

(75) Inventors: Masato Mitsuhashi, Irvine, CA (US);
Hiroko Matsunaga, Kodaira (JP);
Hideki Kambara, Tokyo (JP);
Masafumi Kawamura, Tokyo (JP)

(73) Assignees: Hitachi Chemical Research Center, Inc., Irvine, CA (US); Hitachi Chemical Co., Ltd., Tokyo (JP)

( * ) Notice: Subject to any disclaimer, the term of this patent is extended or adjusted under 35 U.S.C. 154(b) by 441 days.

(21) Appl. No.: 10/297,277

(22) PCT Filed: Jun. 21, 2001

(86) PCT No.: PCT/US01/19980

§ 371 (c)(1),
(2), (4) Date: Apr. 4, 2003

(87) PCT Pub. No.: WO01/98539

PCT Pub. Date: Dec. 27, 2001

(65) Prior Publication Data

US 2003/0215828 A1 Nov. 20, 2003

Related U.S. Application Data

(60) Provisional application No. 60/243,976, filed on Oct. 27, 2000, provisional application No. 60/215,727, filed on Jun. 21, 2000.

(51) Int. Cl.
*C07H 21/04* (2006.01)
*C12Q 1/68* (2006.01)
(52) U.S. Cl. .................. 536/23.1; 536/24.3; 435/6; 435/91.1; 435/91.2
(58) Field of Classification Search .................. None
See application file for complete search history.

(56) References Cited

U.S. PATENT DOCUMENTS 5,272,057 A 12/1993 Smulson et al.

FOREIGN PATENT DOCUMENTS

WO WO 99/47674 9/1999

OTHER PUBLICATIONS

Mali et al., Apr. 1990, J. of Biological Chemistry, vol. 265, p. 6887.*
Result #49 of Seq ID No. 16 search in N_Geneseq database.*
GenBank accession No. BC063704, Dec. 2003.*
Result #6 of Seq ID No. 16 search in GenEmbl database.*
GenBank accession No. L49354, Dec. 1995.*
Result #26 of search of Seq ID No. 16 in GenEmbl database.*
GenBank accession No. AL035408.5, May 1999.*
Result #5 of search of Seq ID No. 16 in GenEmbl database.*
GenBank accession No. AA631033.1, Oct. 1997.*
Result #13 of search of Seq ID No. 16 in EST database.*
Bessho, A., et al. (2000) Detection of Occult Tumor Cells in Peripheral Blood from Patients with Small Cell Lung Cancer by Reverse Transcriptase-Polymerase Chain Reaction. Anticancer Research 20:1149-1154.
Borset, M., et al. (1996) Hepatocyte Growth Factor and Its Receptor c-Met in Multiple Myeloma. Blood 88(10):3998-4004.
Peck, K., et al. (1998) Detection and Quantitation of Circulating Cancer Cells in the Peripheral Blood of Lung Cancer Patients. Cancer Research 58:2761-2765.

* cited by examiner

*Primary Examiner*—Jeanine A. Goldberg
(74) *Attorney, Agent, or Firm*—Knobbe, Martens, Olson & Bear, LLP

(57) ABSTRACT

A method for the diagnosis and identification of new or residual lung cancer is disclosed which uses newly identified markers for lung cancer including syndecan 1, collagen 1 alpha 2, and two novel proteins, 7013 and 7018. The method involves identification of the lung cancer markers is blood from a patient. It is envisioned that at least one marker may be used or any mixture of the four. The method may also include the identification of cytokeratin-19.

11 Claims, 9 Drawing Sheets s-AFLP
Candidate 1
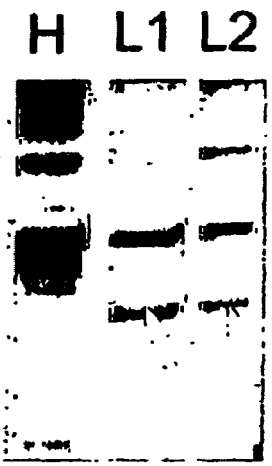
Candidate 2
Candidate 3
Candidate 4
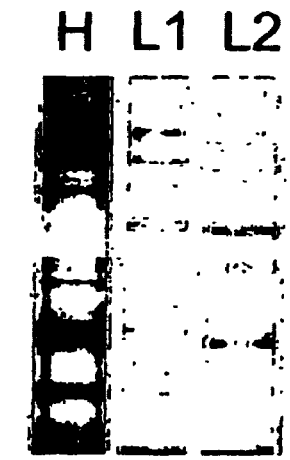
Candidate 5
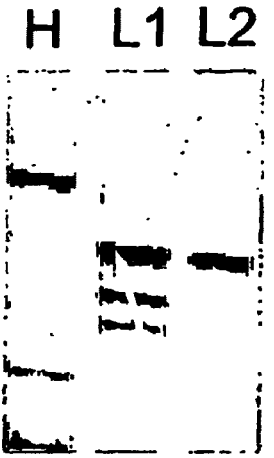
Candidate 6
H: healthy people blood
L: lung cancer tissue
FIG.2

RT-PCR of lung cancer cells syndecan I collagen 1A2

7013   adenocarcinoma
       5807, 2170,
       L185  5800 squamous cell
       carcinoma
7018   H520, 5802 cytokeratin-19

β-actin

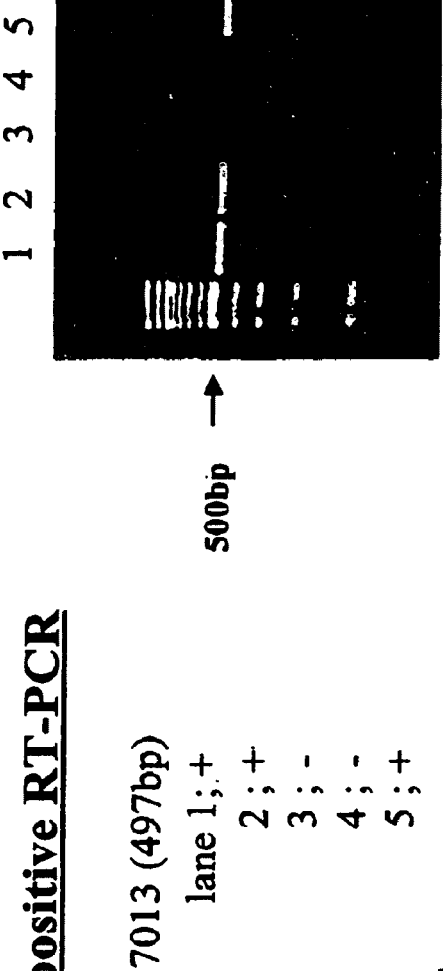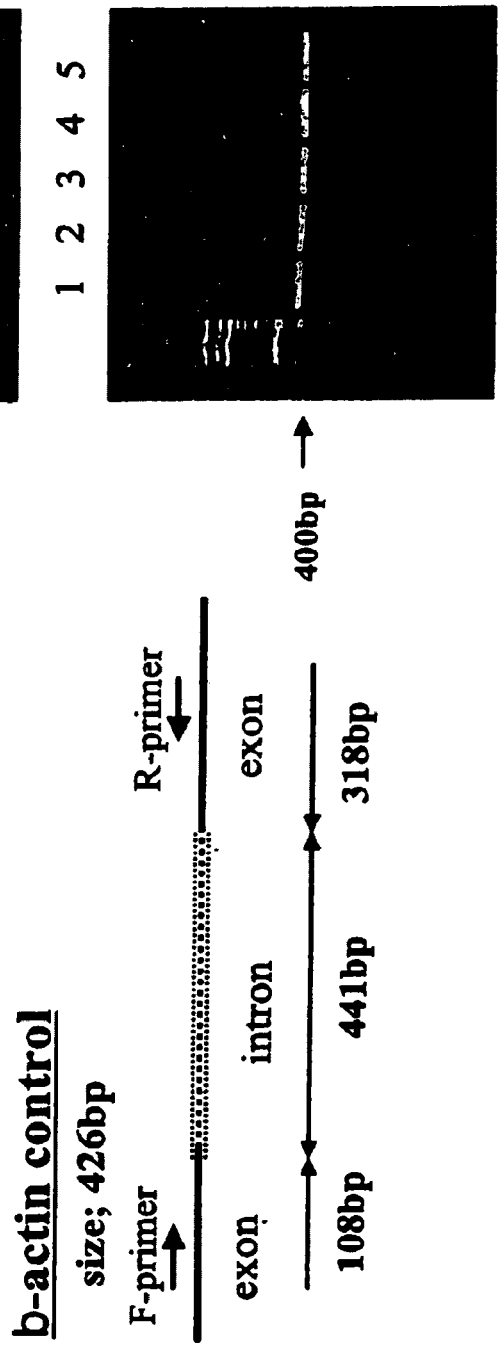
FIG. 5

Syndecan 1 probe tcatgtgtgcaa cagggtatgg actatctgtc tggtggcccc gttctggtgg tctgttggcaggctggccag tccaggctgc cgtggggccg ccgcctcttt caagcagtcg tgcctgtgtccatgcgctca gggccatgct gaggcctggg ccgctgccac gttggagaag cccgtgtgagaagtgaatgc tgggactcag ccttcagaca gagaggactg tagggagggc ggcaggggcctggagatcct cctgcaggct cacgcccgtc ctcctgtggc gccgtctcca ggggctgcttcctcctggaa attgacgagg ggtgtcttgg gcagagctgg ctctgagcgc ctccatccaa ggccaggttc tccgttagct cctgtggccc caccctgggc cctggggctgg aatcaggaat att

FIG. 6

Col probe

5' GGTTTTCTTACAAAGGTTGACATTTTCCTAACAGGNGTAAGA

GTGTTGAAAAAAAATTCAAATTTTTGGGGGAGCGGGGGAA

GGAGTTAATGAAACTGTATTGCACAATGCTCT acaaatgaatg gggaaagaca atcattgaat acaaaacaaa taagccatca cgcctgccct tccttgatat tgcacctttg gacatcggtg gtgctgacca tgaattcttt gtggacattg gcccagtctg tttcaaataa atgaactcaa tctaaattaa aaaagaaaga aatttgaaaa aactttctct ttgccatttc ttcttcttct tttttaactg aaagctgaat accttccatt cttctgcaca tctacttgct taaattgtgg gcaaaagaga aaaagaagga ttgatcagag cattgtgcaa tacagtttca ttaactcctt cccccgc

*FIG. 7*

Probe of 7013

GATCAATGAAGGAG:ACATCTGGAGTGTGCGTGCTTCTTCAGAGGGACGGGT

GATGGGCAGATTGGAAAAAGCACCGCAGATGGGAACCTTAATCTTTCT cacctcccca actcagcact gtctgtctgt gcagcaggtg caaggacgtg ttgaactagc tctctgcagc ctccttggag gatgtgatcc tatgggaggg gtaggagtat tcaggtcctt gacatctccc aaatgtgtga ttccgggatg ccaaaggcct ttggccaggt aatgcagtgt ctacaggctg aggttgacat gcatccccac cctctgagaa aaagatcctc agacaatcca tgtgcttctc ttgtccttca ttccaccgga gtctgtctca tacccaacca gatttcagtg gagtgaagtt caggaggcat ggagctgaca accatgaggc ctcggcagcc accgccacca ccgccgccgc caccaccgta gcagcagcag cagcagcagc agcagcagca gcagcagcaa gagtaactct gacttaggaa tagagacagc cagagagaaa tgtgatcaat gaaggagaca tctggagtgt

*FIG.8*

Probe of 7018

ATCCATGCACGTCACTTTCCTTTCCACTGGGCAGGATAGCCGAGCACACTC
CCTCCTGCGCTCTCCCGCCCCGGTGCGTCCACTCCCGAGGGCTGTTATGAG
GACTGGGTTGTGCCTACTTGACTTCCTGCAAAAAAAAAAAAAAAAAAA ggcaggatag ccaagcacac tccctcctgc gctctcccgc cccggtgcgt ccactcccga
gggctgttat gaggactggg ttgtgcctac ttgatttgaa aacacacaca agcaataaaa
agcctcttcc tgcattgtct gtggtgtgac catagcagat tatatttggt tcctgaatgt
ttgtggtgct aatttctgtg tttgttccaa gccgttcagt catgccatgc gctgcctcgg
tagatggagt aatgtacaat gaactccatg agtctctcca gggctgcctg cagcacgtct
tttacaagta gcctatttgg attcccatct caaatgtcct ggatgcgagc gtcagcgggt
ccagagctcg gggcgggtga ggtccccttt ggggaaccct ttcctggcca tctaggtcgg
ggggctgcct tctgtgggca ggaggac

*FIG. 9*

```
                           SEQUENCE LISTING

<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: Linker Oligomer  P1.

<400> SEQUENCE: 1
gatcccctat agtgagtc                                                       18

<210> SEQ ID NO 2
<211> LENGTH: 14
<212> TYPE: DNA
<213> ORGANISM: Artificial Sequence
<220> FEATURE:
<223> OTHER INFORMATION: Helper Oligomer  P2.

<400> SEQUENCE: 2
gactcactat aggg                                                           14

<210> SEQ ID NO 3
<211> LENGTH: 19
<212> TYPE: DNA
<213> ORGANISM: Artificial Sequence
<220> FEATURE:
<223> OTHER INFORMATION: Degenerate Primer P3.
<220> FEATURE:
<221> NAME/KEY: misc_feature
<222> LOCATION: (1)...(19)
<223> OTHER INFORMATION: n = A,T,C or G

<400> SEQUENCE: 3
gactcactat agggatcnn                                                      19

<210> SEQ ID NO 4
<211> LENGTH: 25
<212> TYPE: DNA
<213> ORGANISM: Artificial Sequence
<220> FEATURE:
<223> OTHER INFORMATION: anchor primer P4.
<220> FEATURE:
<221> NAME/KEY: misc_feature
<222> LOCATION: (1)...(25)
<223> OTHER INFORMATION: n = A,T,C or G

<400> SEQUENCE: 4 tctcctttt ttttttttt tttvn                                                 25
```

```
<210> SEQ ID NO 5
<211> LENGTH: 20
<212> TYPE: DNA
<213> ORGANISM: Artificial Sequence
<220> FEATURE:
<223> OTHER INFORMATION: SYND primer P5.

<400> SEQUENCE: 5
tcatgtgtgc aacagggtat                                                 20

<210> SEQ ID NO 6
<211> LENGTH: 20
<212> TYPE: DNA
<213> ORGANISM: Artificial Sequence
<220> FEATURE:
<223> OTHER INFORMATION: SYND primer P6

<400> SEQUENCE: 6
aatattcctg attccagccc                                                 20

<210> SEQ ID NO 7
<211> LENGTH: 33
<212> TYPE: DNA
<213> ORGANISM: Artificial Sequence
<220> FEATURE:
<223> OTHER INFORMATION: COL primer P7

<400> SEQUENCE: 7
agagcattgt gcaatacagt ttcattaact cct                                  33

<210> SEQ ID NO 8
<211> LENGTH: 34
<212> TYPE: DNA
<213> ORGANISM: Artificial Sequence
<220> FEATURE:
<223> OTHER INFORMATION: COL primer P8.

<400> SEQUENCE: 8
ggttttctta caaaggttga cattttccta acag                                 34

<210> SEQ ID NO 9
<211> LENGTH: 26
<212> TYPE: DNA
<213> ORGANISM: Artificial Sequence
<220> FEATURE:
<223> OTHER INFORMATION: 7013 Primer P9.

<400> SEQUENCE: 9
aatgaaggag acatctggag tgtgcg                                          26

<210> SEQ ID NO 10
<211> LENGTH: 30
<212> TYPE: DNA
<213> ORGANISM: Artificial Sequence
<220> FEATURE:
<223> OTHER INFORMATION: 7013 Primer P10.

<400> SEQUENCE: 10
agaaaagaaa gattaaggtt cccatctgcg                                      30

<210> SEQ ID NO 11
<211> LENGTH: 25
<212> TYPE: DNA
<213> ORGANISM: Artificial Sequence
<220> FEATURE:
<223> OTHER INFORMATION: 7018 Primer P11.
```

<400> SEQUENCE: 11
atccatgcac gtcactttcc tttcc                                         25

<210> SEQ ID NO 12
<211> LENGTH: 23
<212> TYPE: DNA
<213> ORGANISM: Artificial Sequence
<220> FEATURE:
<223> OTHER INFORMATION: 7018 Primer P12.

<400> SEQUENCE: 12
tcaagtaggc acaacccagt cct                                           23

<210> SEQ ID NO 13
<211> LENGTH: 24
<212> TYPE: DNA
<213> ORGANISM: Artificial Sequence
<220> FEATURE:
<223> OTHER INFORMATION: CK-19 Primer P13.

<400> SEQUENCE: 13
caagatcctg agtgacatgc gaag                                          24

<210> SEQ ID NO 14
<211> LENGTH: 22
<212> TYPE: DNA
<213> ORGANISM: Artificial Sequence
<220> FEATURE:
<223> OTHER INFORMATION: CK-19 Primer P14.

<400> SEQUENCE: 14
cgctgatcag cgcctggata tg                                            22

<210> SEQ ID NO 15
<211> LENGTH: 18
<212> TYPE: DNA
<213> ORGANISM: Artificial Sequence
<220> FEATURE:
<223> OTHER INFORMATION: T7 Primer.

<400> SEQUENCE: 15
taatacgact cactatag                                                 18

<210> SEQ ID NO 16
<211> LENGTH: 490
<212> TYPE: DNA
<213> ORGANISM: Artificial Sequence
<220> FEATURE:
<223> OTHER INFORMATION: 7013 probe.

<400> SEQUENCE: 16
cacctcccca actcagcact gtctgtctgt gcagcaggtg caaggacgtg ttgaactagc    60
tctctgcagc ctccttggag gatgtgatcc tatgggaggg gtaggagtat tcaggtcctt   120
gacatctccc aaatgtgtga ttccgggatg ccaaaggcct ttggccaggt aatgcagtgt   180
ctacaggctg aggttgacat gcatccccac cctctgagaa aaagatcctc agacaatcca   240
tgtgcttctc ttgtccttca ttccaccgga gtctgtctca tacccaacca gatttcagtg   300
gagtgaagtt caggaggcat ggagctgaca accatgaggc ctcggcagcc accgccacca   360
ccgccgccgc caccaccgta gcagcagcag cagcagcagc agcagcagca gcagcagcaa   420
gagtaactct gacttaggaa tagagacagc cagagagaaa tgtgatcaat gaaggagaca   480
tctggagtgt                                                         490

<210> SEQ ID NO 17
<211> LENGTH: 447
<212> TYPE: DNA
<213> ORGANISM: Artificial Sequence
<220> FEATURE:
<223> OTHER INFORMATION: 7018 probe.

<400> SEQUENCE: 17

| | | | | | |
|---|---|---|---|---|---|
| ggcaggatag | ccaagcacac | tccctcctgc | gctctcccgc | cccggtgcgt | ccactcccga | 60 |
| gggctgttat | gaggactggg | ttgtgcctac | ttgatttgaa | acacacaca | agcaataaaa | 120 |
| agcctcttcc | tgcattgtct | gtggtgtgac | catagcagat | tatatttggt | tcctgaatgt | 180 |
| ttgtggtgct | aatttctgtg | tttgttccaa | gccgttcagt | catgccatgc | gctgcctcgg | 240 |
| tagatggagt | aatgtacaat | gaactccatg | agtctctcca | gggctgcctg | cagcacgtct | 300 |
| tttacaagta | gcctatttgg | attcccatct | caaatgtcct | ggatgcgagc | gtcagcgggt | 360 |
| ccagagctcg | gggcgggtga | ggtccccttt | ggggaaccct | ttcctggcca | tctaggtcgg | 420 |
| ggggctgcct | tctgtgggca | ggaggac | | | | 447 |

<210> SEQ ID NO 18
<211> LENGTH: 2484
<212> TYPE: DNA
<213> ORGANISM: Homo sapiens

<400> SEQUENCE: 18

| | | | | | |
|---|---|---|---|---|---|
| ggcacgagga | agggcctgtg | ggtttattat | aaggcggagc | tcggcgggag | aggtgcgggc | 60 |
| cgaatccgag | ccgagcggag | aggaatccgg | cagtagagag | cggactccag | ccggcggacc | 120 |
| ctgcagccct | cgcctgggac | agcggcgcgc | tgggcaggcg | cccaagagag | catcgagcag | 180 |
| cggaacccgc | gaagccggcc | cgcagccgcg | acccgcgcag | cctgccgctc | tcccgccgcc | 240 |
| ggtccgggca | gcatgaggcg | cgcggcgctc | tggctctggc | tgtgcgcgct | ggcgctgagc | 300 |
| ctgcagccgg | ccctgccgca | aattgtggct | actaatttgc | ccctgaaga | tcaagatggc | 360 |
| tctggggatg | actctgacaa | cttctccggc | tcaggtgcag | gtgctttgca | agatatcacc | 420 |
| ttgtcacagc | agaccccctc | cacttggaag | gacacgcagc | tcctgacggc | tattcccacg | 480 |
| tctccagaac | ccaccggcct | ggaggctaca | gctgcctcca | cctccaccct | gccggctgga | 540 |
| gaggggccca | aggagggaga | ggctgtagtc | ctgccagaag | tggagcctgg | cctcaccgcc | 600 |
| cgggagcagg | aggccacccc | ccgacccagg | gagaccacac | agctcccgac | cactcatcag | 660 |
| gcctcaacga | ccacagccac | cacggcccag | gagcccgcca | cctcccaccc | cacagggac | 720 |
| atgcagcctg | gccaccatga | gacctcaacc | cctgcaggac | ccagccaagc | tgaccttcac | 780 |
| actccccaca | cagaggatgg | aggtccttct | gccaccgaga | gggctgctga | ggatggagcc | 840 |
| tccagtcagc | tccagcagca | agagggctct | ggggagcagg | acttcacctt | tgaaacctcg | 900 |
| ggggagaata | cggctgtagt | ggccgtggag | cctgaccgcc | ggaaccagtc | cccagtggat | 960 |
| caggggggcca | cgggggcctc | acagggcctc | ctggacagga | aagaggtgct | gggaggggtc | 1020 |
| attgccgtag | gcctcgtggg | gctcatcttt | gctgtgtgcc | tggtgggttt | catgctgtac | 1080 |
| cgcatgaaga | agaaggacga | aggcagctac | tccttggagg | agccgaaaca | agccaacggc | 1140 |
| ggggcctacc | agaagcccac | caaacaggag | gaattctatg | cctgacgcgg | gagccatgcg | 1200 |
| cccccctccgc | cctgccactc | actaggcccc | cacttgcctc | ttccttgaag | aactgcaggc | 1260 |
| cctggcctcc | cctgccacca | ggccacctcc | ccagcattcc | agccctctg | gtcgctcctg | 1320 |

-continued

```
cccacggagt cgtggggtgt gctgggagct ccactctgct tctctgactt ctgcctggag    1380
acttagggca ccagggggttt ctcgcatagg acctttccac cacagccagc acctggcatc    1440
gcaccattct gactcggttt ctccaaactg aagcagcctc tccccaggtc cagctctgga    1500
ggggaggggg atccgactgc tttggaccta aatggcctca tgtggctgga agatcctgcg    1560 ggtgggggctt gggctcaca cacctgtagc acttactggt aggaccaagc atcttggggg    1620
ggtggccgct gagtggcagg ggacaggagt ccactttgtt tcgtggggag gtctaatcta    1680
gatatcgact tgttttttgca catgtttcct ctagttcttt gttcatagcc cagtagacct    1740
tgttacttct gaggtaagtt aagtaagttg attcggtatc cccccatctt gcttccctaa    1800
tctatggtcg ggagacagca tcagggttaa gaagactttt ttttttttttt tttttaaact    1860 aggagaacca aatctggaag ccaaaatgta ggcttagttt gtgtgttgtc tcttgagttt    1920
gtcgctcatg tgtgcaacag ggtatggact atctgtctgg tggccccgtt tctggtggtc    1980
tgttggcagg ctggccagtc caggctgccg tggggccgcc gcctctttca agcagtcgtg    2040
cctgtgtcca tgcgctcagg gccatgctga ggcctgggcc gctgccacgt tggagaagcc    2100
cgtgtgagaa gtgaatgctg ggactcagcc ttcagacaga gaggactgta gggagggcgg    2160
caggggcctg gagatcctcc tgcagaccac gcccgtcctg cctgtggcgc cgtctccagg    2220
ggctgcttcc tcctggaaat tgacgagggg tgtcttgggc agagctggct ctgagcgcct    2280
ccatccaagg ccaggttctc cgttagctcc tgtggcccca ccctgggccc tgggctggaa    2340
tcaggaatat tttccaaaga gtgatagtct tttgcttttg gcaaaactct acttaatcca    2400
atgggttttt ccctgtacag tagattttcc aaatgtaata aactttaata taaagtaaaa    2460
aaaaaaaaaa aaaaaaaaaa aaaa                                            2484
```

<210> SEQ ID NO 19
<211> LENGTH: 310
<212> TYPE: PRT
<213> ORGANISM: Homo sapiens

<400> SEQUENCE: 19

```
Met Arg Arg Ala Ala Leu Trp Leu Trp Leu Cys Ala Leu Ala Leu Ser
  1               5                  10                  15

Leu Gln Pro Ala Leu Pro Gln Ile Val Ala Thr Asn Leu Pro Pro Glu
             20                  25                  30

Asp Gln Asp Gly Ser Gly Asp Asp Ser Asp Asn Phe Ser Gly Ser Gly
         35                  40                  45

Ala Gly Ala Leu Gln Asp Ile Thr Leu Ser Gln Gln Thr Pro Ser Thr
     50                  55                  60

Trp Lys Asp Thr Gln Leu Leu Thr Ala Ile Pro Thr Ser Pro Glu Pro
 65                  70                  75                  80

Thr Gly Leu Glu Ala Thr Ala Ala Ser Thr Ser Thr Leu Pro Ala Gly
                 85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Gln Ala Ser Thr Thr Ala Thr Thr
    130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
```

```
                      165                 170                 175
Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
    210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Val Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
    290                 295                 300

Gln Glu Glu Phe Tyr Ala
305                 310

<210> SEQ ID NO 20
<211> LENGTH: 172
<212> TYPE: DNA
<213> ORGANISM: Homo sapiens

<400> SEQUENCE: 20
aggtccacat ggccccgtgg gtcctgctgg caaacatggt aaccgtggtg taactggtcc      60
ttctggtcct gttggtcctg ctggtgctgt tggcccaaga ggtcctagtg gcccacaagg     120
cattcgtggc gataagggag agcccggtga aaaggggccc agaggtcttc ct             172

<210> SEQ ID NO 21
<211> LENGTH: 56
<212> TYPE: PRT
<213> ORGANISM: Homo sapiens

<400> SEQUENCE: 21

Gly Pro His Gly Pro Val Gly Pro Ala Gly Lys His Gly Asn Arg Gly
1               5                   10                  15

Val Thr Gly Pro Ser Gly Pro Val Gly Pro Ala Gly Ala Val Gly Pro
            20                  25                  30

Arg Gly Pro Ser Gly Pro Gln Gly Ile Arg Gly Asp Lys Gly Glu Pro
        35                  40                  45

Gly Glu Lys Gly Pro Arg Gly Leu
    50                  55

<210> SEQ ID NO 22
<211> LENGTH: 425
<212> TYPE: DNA
<213> ORGANISM: Artificial Sequence
<220> FEATURE:
<223> OTHER INFORMATION: Syndecan 1 probe.

<400> SEQUENCE: 22
tcatgtgtgc aacagggtat ggactatctg tctggtggcc ccgttctggt ggtctgttgg      60
caggctggcc agtccaggct gccgtggggc cgccgcctct ttcaagcagt cgtgcctgtg     120
tccatgcgct cagggccatg ctgaggcctg ggccgctgcc acgttggaga agcccgtgtg     180
```

```
agaagtgaat gctgggactc agccttcaga cagagaggac tgtagggagg gcggcagggg      240
cctggagatc ctcctgcagg ctcacgcccg tcctcctgtg gcgccgtctc cagggctgc      300 ttcctcctgg aaattgacga ggggtgtctt gggcagagct ggctctgagc gcctccatcc      360
aaggccaggt tctccgttag ctcctgtggc cccaccctgg gcctgggct ggaatcagga      420 atatt                                                                 425

<210> SEQ ID NO 23
<211> LENGTH: 337
<212> TYPE: DNA
<213> ORGANISM: Artificial Sequence
<220> FEATURE:
<223> OTHER INFORMATION: Collagen Pro alpha 2  probe.

<400> SEQUENCE: 23
acaaatgaat gggaaagaca atcattgaat acaaaacaaa taagccatca cgcctgccct      60
tccttgatat tgcacctttg gacatcggtg gtgctgacca tgaattcttt gtggacattg      120
gcccagtctg tttcaaataa atgaactcaa tctaaattaa aaagaaaga aatttgaaaa       180 aactttctct ttgccatttc ttcttcttct tttttaactg aaagctgaat ccttccattt      240
cttctgcaca tctacttgct taaattgtgg gcaaagaga aaaagaagga ttgatcagag       300
cattgtgcaa tacagtttca ttaactcctt cccccgc                              337

<210> SEQ ID NO 24
<211> LENGTH: 115
<212> TYPE: DNA
<213> ORGANISM: Artificial Sequence
<220> FEATURE:
<223> OTHER INFORMATION: Collagen Pro alpha 2  probe.
<220> FEATURE:
<221> NAME/KEY: misc_feature
<222> LOCATION: (1)...(115)
<223> OTHER INFORMATION: n = A,T,C or G

<400> SEQUENCE: 24
ggttttctta caaaggttga catttttccta acaggngtaa gagtgttgaa aaaaaaattc     60
aaatttttgg gggagcgggg gaaggagtta atgaaactgt attgcacaat gctct          115

<210> SEQ ID NO 25
<211> LENGTH: 99
<212> TYPE: DNA
<213> ORGANISM: Artificial Sequence
<220> FEATURE:
<223> OTHER INFORMATION: 7013  probe.

<400> SEQUENCE: 25
gatcaatgaa ggagacatct ggagtgtgcg tgcttcttca gagggacggg tgatgggcag     60
attggaaaaa gcaccgcaga tgggaacctt aatctttct                            99

<210> SEQ ID NO 26
<211> LENGTH: 149
<212> TYPE: DNA
<213> ORGANISM: Artificial Sequence
<220> FEATURE:
<223> OTHER INFORMATION: 7018  probe.
```

<400> SEQUENCE: 26

```
atccatgcac gtcactttcc tttccactgg gcaggatagc cgagcacact ccctcctgcg      60
ctctccccgc cccggtgcgt ccactcccga gggctgttat gaggactggg ttgtgcctac     120
ttgacttcct gcaaaaaaaa aaaaaaaa                                        149
```

GENE MARKERS FOR LUNG CANCER

This application is the U.S. National Phase under 35 U.S.C. §371 of International Application PCT/US01/19980, filed Jun. 21, 2001, which claims priority to U.S. Provisional Application Nos. 60/215,727 filed Jun. 21, 2000, and 60/243,976 filed Oct. 27, 2000. The International Application was published under PCT Article 21(2) in English.

FIELD OF THE INVENTION

The invention relates to a method for the diagnosis and identification of residual lung cancer. The invention further relates to the use of newly identified cellular markers for lung cancer. These markers include syndecan 1, collagen 1 alpha 2, and two novel proteins, 7013 and 7018.

BACKGROUND OF THE INVENTION

Lung cancer is one of the most common cancers in industrial nations and has an extremely high mortality rate. Early diagnosis and effective treatments are not available at this time. A chest X-ray is frequently used for lung cancer screening, however, it is not useful for the detection of early stage cancer. CT scans may also be used and may allow detection of the cancer at an earlier stage, however, this procedure takes time and has a risk of exposure.

Cancer cells or micrometastases are frequently detected in the blood stream of patients with melanomas, thyroid cancers, and prostate cancers. Currently reverse transcription-based polymerase chain reaction (RT-PCR) is a powerful method capable of detecting a single cancer cell within millions of normal blood cells by amplifying a cancer specific gene or marker. This makes RT-PCR detection of micrometastases a promising diagnostic procedure for the prognosis, choice of appropriate treatments, and monitoring of the efficacy of each treatment. Furthermore, blood tests do not induce any health hazards, whereas methods such as X-ray or CT scan do. In addition, blood tests cause very minor physical discomfort as compared to endoscopic examination and biopsy. Lung cancer frequently induces blood-born metastasis even in the early stages—before symptomatic disease and many lung cancers relapse as distant metastases, such as in brain, bone, and liver. This is due to the lung cancer induced blood-borne metastasis. This knowledge can be used, however, because it suggests that the diagnosis and detection of relapse could be made on the basis of these blood borne metastases at a very early stage. However, there are no good markers available for the identification of the metastatic lung cancers cells in the blood. Currently, lung cancer markers such as cytokeratin-19 and CEA are used for the diagnosis of non-small cell lung cancer by RT-PCR (reverse transcriptase polymerase chain reaction) but lack specificity, and result in a high number of false positives and negatives.

RT-PCR of micrometastases, then, is especially advantageous for the detection of lung cancer due to the large patient population, high incidence of blood-borne metastasis, poor prognosis, and high medical cost for advanced cancer treatments. In addition, specific antibodies are not available as of yet for lung cancer.

Therefore, specific markers and a method of diagnosis of lung cancer by detecting blood-borne metastasis is needed.

SUMMARY OF THE INVENTION

One embodiment is a method for the identification of lung cancer by isolating blood or non-lung tissue from a patient, and identifying the presence of at least one marker from the following: syndecan 1, collagen 1 alpha 2, 7013, and 7018. The method may also include identifying the presence of the marker cytokeratin-19. In a further embodiment at least two markers are identified. In a further embodiment more than two markers are identified. The method of identification may be any known to one of skill in the art, but may also include RT-PCR and/or antibody binding. The patient may be any living thing, but in one embodiment is a mammal, particularly a human, dog, or cat.

A further embodiment is a method for the isolation or removal of metastatic cancer cells, by treating cells or a non-lung tissue containing cancer cells with antibodies specific for at least one marker selected from the group consisting of: syndecan 1, collagen 1 alpha 2, 7013, and 7018. The method may also include antibodies specific for the marker cytokeratin-18. In one embodiment, the antibodies are bound to a moiety selected from the group consisting of metallic particles, fluorescent particles, chromatography beads, a chromatography gel and a solid support. In a further embodiment, two markers are used. In a further embodiment more than two markers are used.

A further embodiment is a polynucleotide comprising at least 17 nucleotides of SEQ ID NO: 16 (deposited as ATCC PTA-3471, Jun. 21, 2001) also identified herein as marker 7013. A further embodiment is at least 17 nucleotides of the polynucleotide deposited as ATCC PTA-3473, Jun. 21, 2001.

A further embodiment is a polynucleotide comprising at least 17 nucleotides of SEQ ID NO: 17 (deposited as ATCC PTA-3472, Jun. 21, 2001) also identified herein as marker 7018.

A further embodiment is a method for the identification of metastases of a solid tumor in a patient by, isolating blood or bone marrow from said patient; and identifying the presence of at least one marker selected from the group consisting of: syndecan 1, collagen 1 alpha 2, 7013, and 7018. The method may also include identifying cytokeratin-18. In one embodiment, the solid tumor is selected from the group consisting of bile duct, colon, breast, uterus, esophagus, and larynx.

A further embodiment is a method for the identification of a carcinoma, by obtaining a cancer cell; and identifying the presence of the markers selected from the group consisting of: 7013, 7018, and both.

BRIEF DESCRIPTION OF THE DRAWINGS

FIG. 2 is a polyacrylamide gel showing 6 candidate bands which were more abundant in the lung cancer RNA than in either normal blood lane. H: healthy people, L: Lung cancer tissue.

FIG. 5 is an example of a positive PCR and a negative PCR from blood RNA.

FIG. 6 is the sequence information for Syndecan 1 probe (SEQ ID NO: 22).

FIG. 7 is the sequence information for Collagen-1 Pro alpha 2 115 nt fragment (SEQ ID NO: 24) as well as the 337 nt probe sequence (SEQ ID NO: 23).

FIG. 8 is the sequence information for the 7013 gene (SEQ ID NO: 16) as well as the probe sequence (SEQ ID NO: 25).

FIG. 9 is the sequence information for 7018 gene (SEQ ID NO: 17) as well as the probe sequence (SEQ ID NO: 26).

DETAILED DESCRIPTION OF THE PREFERRED EMBODIMENT

Figure 1:
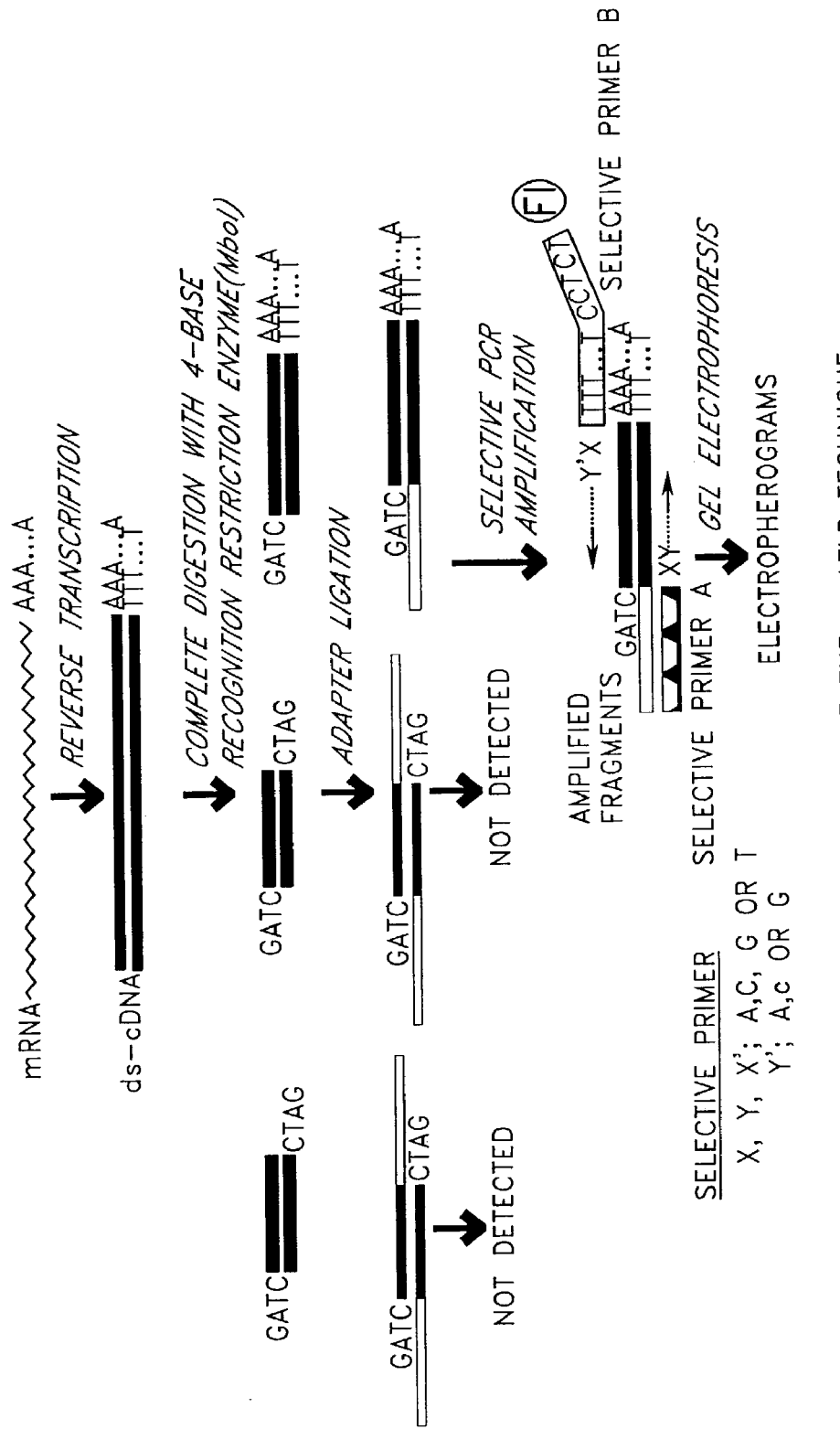
FIG. 1 is a representation of the modified differential display procedure, selective-Amplified Fragment Length Polymorphism method (s-AFLP) used in the preferred embodiment.

Differential display was used to identify mRNA's specifically expressed by lung cancer cells which circulate in the blood and are not expressed by normal blood cells. The differential display method was modified from the classical procedure to allow a more comprehensive representation of the genes expressed in a cell.

In order to identify candidate genes, three major technologies are presently available: subtraction libraries, differential display, and DNA microchip arrays. However, subtraction libraries, though being potentially useful, may also identify genes which exhibit partial similarity in gene sequences and is a very laborious and time intensive technique. DNA microchip arrays, though quick and easy to do, are not sensitive enough to detect rare genes in blood samples. This is particularly important because the method needs to be able to detect rare micrometastases which express specific markers within a large background (millions of white blood cells) of normal cells which do not. Differential display (dd-PCR) allows for the amplification of all existing genes using combinations of multiple degenerate primers, thus increasing the likelihood that a rare marker or gene will be detected.

However, in order to improve the differential display technology to represent as many genes as possible, selective Amplified Fragment Length Polymorphism (s-AFLP) was used in Example 1. This approach has the advantages of 1) amplifying only the 3' end of the gene, 2) producing more reproducible gel patterns, 3) identifying fewer redundant genes, and 4) using more selective PCR conditions. The method resulted in the identification of 4 markers: Synd, Col, 7013 and 7018.

These markers may be used to identify lung cancer cells in the blood of a patient at any stage of disease. Any method known to one of skill in the art may be used to identify the markers in the blood or in any metastatic tissue. For example, the mRNA expressed by the cells which is specific to the markers may be identified.

Alternatively, the proteins themselves may be identified using immuno-techniques, such as Western blot, FACS technology, ELISA, and other methods known to one of skill in the art. The antibodies or functional antibody parts may be purchased, isolated, or produced using known methods.

In one embodiment, the gene expression of the marker is identified. Any method which allows for identification of expression of the gene associated with the marker can be used. Typically, the method amplifies the mRNA resulting from expression of the gene. In one embodiment, RT-PCR of the mRNA from blood or tissue is used. In a further embodiment, antibodies are used to identify cells in the blood containing these markers. For example, cell sorting can be used to identify cells which have been fluorescently labeled with antibodies to these markers.

In one embodiment, the method is used to identify the presence of lung cancer cells in the blood or bone marrow. However, it can be envisioned that mRNA from any tissue which does not normally produce these markers may be used. For example, the mRNA from an organ which is typically the site of metastases can be used. Therefore, in a further embodiment, the method is used to identify lung cancer cells in an organ such as liver or brain.

In one embodiment, the method is used to identify the presence of lung cancer cells at a very early stage in the disease, in a further embodiment, the lung cancer cells are identified after remission or to identify a relapse.

In a further embodiment, the markers are used to target the lung cancer cells in vivo or in vitro. In one embodiment, the body is cleared of cancer cells using affinity techniques which allow the cancer cells to be targeted and removed from the blood.

In a further embodiment, the markers are used to identify metastatic cells in the blood or bone marrow or a metastatic organ or tissue which are produced by such cancers as bile duct, colon, breast, uterus, esophagus, and larynx. The markers may alternatively be used to remove the metastatic cells from blood.

In a further embodiment, the markers, 7013 and 7018 are used to identify whether a cancer cell or other cell is of epithelial origin. For example, if the cell expresses one or both markers, it is likely of epithelial origin.

The patient may be any animal which is capable of having cancer. In one embodiment, the patient is a mammal. In a further embodiment, the mammal is a pet, such as a dog or cat. In a further embodiment, the patient is a human.

The invention will now be explained with reference to the Examples below. However, it is understood that these examples merely illustrate, but do not restrict the invention.

In Examples 1 and 2, the markers are identified using a variant of the differential display technique. The markers which are identified are explained in Example 2.

EXAMPLE 1 s-AFLP Differential Display s-AFLP is based on the selective PCR amplification of restriction fragments from a cDNA library. Two sets of selective primers were used. The first one, selective primer A in FIG. 1, consisted of three parts; a core sequence, an enzyme specific sequence and two selective nucleotides at the 3' termini. This provided for $4^2=16$ kinds of primers because of the variation of selective sequences. The second one, selective primer B in FIG. 1, also consisted of three parts: an anchor sequence, a poly T sequence and two selective nucleotides at the 3' termini which are fluorophore labelled. This then provided for $3\times4=12$ kinds of primers, because of the 3 selective sequences following the poly T (A, G, and C). Thus, all of the 3' terminal cDNA restriction fragments including a poly A region were included in the 192 ($16\times12$) groups produced by this method of selective PCR. Each signal on the gel display of amplified fragments indicated a non-overlapping gene in the cDNA library. Using this technique, RNA isolated from lung cancer specimens was compared with RNA from the blood of healthy individuals. Differentially expressed genes, which were overexpressed in the cancer specimens, were considered candidates for general genetic markers for tumor cell dissemination.

For successful s-AFLP, excellent quality RNA was important. However, lung specimens are one of the most difficult tissues to prepare RNA from due to the presence of abundant Rnases from alveolar macrophages. Therefore, snap frozen lung cancer specimens were purchased from NCCRI (Chuou-ku, Tokyo, Japan) and total RNA was purified by the AGPC method as previously described (Tominaga, K, Miura, Y. Arakawa, T. Koboyashi, K. and Mitsuhashi, M. Clin. Chem., 42, 1750–1783, 1998). Agarose gel electrophoresis or a micro-capillary chip was used to assess the quality of the RNA and to confirm the presence of two rRNA bands. Acceptable specimens were then used for s-AFLP. Six lung cancer specimens were used and each sample was derived from different patients. Four of six were adenocarcinoma and two were squamous cell carcinoma. Twenty control bloods were derived from healthy volunteers with no history or present diagnosis of malignancy or other diseases.

Total RNA Preparation of Tumor and Blood Specimens

Fresh frozen tumor specimens were broken into small pieces in liquid nitrogen. Total RNA was extracted from 100 mg specimen by the guanidine method (Chomzynski, P. and Sacchi, N. 1987. Single-step method of RNA isolation by acid guanidine thiocyanate-phenol-chloroform extraction. Anal. Biochem. 162:156–159). Peripheral blood samples were collected from the veins of the patients and healthy volunteers in heparin anticoagulant containing tubes. Two samples were collected from each subject, with 1–2 ml of peripheral blood in the first tube and 10 ml in the second tube. The first tube was discarded because it could have been contaminated with epithelial cells picked up by the needle when it pierced the skin, and only the second tube was assayed. Total RNA was extracted from peripheral blood samples with RiboCap™ (RNature, Irvine, Calif.) according to the manufacturer's instructions. Purified total RNA qualities were checked by agarose gel electrophoresis with 18s and 28s ribosomal RNA bands and their quantity were measured by UV spectrometer.

Differential Display s-AFLP Analysis

A modified differential, "s-AFLP" was carried out using a selective primer technique.

Six lung cancer specimens (lung cancer tissue) and two pooled healthy blood samples that contained 5 healthy individuals each were used for s-AFLP analysis. All oligomers used in the whole assay were obtained from Sawady Technology (Tokyo, Japan). Double stranded cDNAs were synthesized from 30 μg of total RNA. Following denaturation for 5 min at 65° C., RNA was reverse-transcribed for 90 min at 37° C. in a 50 μl reaction mix which contained the following: 50 μg/ml of oligo(dT)$_{12-18}$ primer (Life Technologies, USA), 500 μM of each deoxynucleotide triphosphate (dNTP) (Life Technologies), 50 mM of Tris-HCl (pH 8.3), 75 mM of KCl, 3 mM of MgCl$_2$, 10 mM of dithiothreitol (DTT), 20 units of RNAsin (Life Technologies), and 10,000 units/ml of MMLV Reverse Transcriptase (Life Technologies). Second strand reactions were performed for 120 min at 16° C. by adding the following components for the final concentrations; 25 mM Tris-HCl (pH 8.3), 100 mM KCl, 10 mM (NH$_4$)$_2$SO$_4$, 5 mM MgCl$_2$, 250 μM 0f each dNTP, 0.15 mM NAD, 5 mM DTT, 250 units/ml of DNA polymerase (Life Technologies), and 30 units/ml of DNA ligase (Life Technologies). After the reaction, the tube was placed on ice and 12.5 μl of 0.25 M ethlenediaminetetraaceticacid (EDTA; pH 7.5) was added for enzyme inactivation. The product was extracted with phenol/chloroform once and ethanol precipitated. Double stranded cDNA was digested with X units 4-base recognition restriction enzyme MboI (↓ GATC; New England Biolabs, USA) for 60 minutes at 37° C. The phosphate residue at the 5' termini of digested fragments was removed with calf intestinal alkaline phosphatase (CIAP; Takara, Japan) to avoid self-ligation during the ligation process. 20 units of CIAP and 10 μl of 10× alkaline phosphate buffer (500 mM Tris-HCl (pH 9.0), 10 mM MgCl$_2$) was added and incubated for 30 minutes at 37° C. The product was extracted with phenol/chloroform twice and ethanol precipitated. Fragments were ligated to the oligomers to introduce priming sites.

The following oligomers were used for ligation: (P1) 5'-P-GATCCCCTATAGTGAGTC-3' (linker oligomer) [SEQ ID NO:1]; (P2) 5'GACTCACTATAGGG-P-3' (helper oligomer)[SEQ ID NO:2]. The helper oligomer was phosphorylated at the 3'-terminal end to prevent the production of oligomer dimers. The ligation reaction was performed with 1:100:200 molar ratio of the digested fragments to helper oligomer to linker oligomer.

The reaction was performed by adding 15 μl of Ligation High (Toyobo) in a 45 μl reaction at 16° C. overnight. After removal of unligated oligomer by QIAquick Nucleotide Removal Kit (Qiagen, Germany), the fragments of 3' terminus including the poly A tailing were amplified and detected using two types of selective primers. One of them (P3) consisted of three parts: a complementary sequence of anchor oligomer, an MboI recognition sequence (GATC) and two degenerate nucleotides at the 3' termini (5'-GACTCAC-TATAGGGATCNN-3')[SEQ 10 NO:3]. P3 has $4^2=16$ types because of the variation of selective sequences (NN). A second selective primer (P4) also consisted of three parts: an anchor sequence, a poly T sequence and two degenerate nucleotides at the 3' termini labelled with a sulforhodamine 101 label (5'-TCTCCTTTTTTTTTTTTTTTTTTVN-3') [SEQ ID NO:4]. P4 has 3×4=12 types, because the selective sequence "V" is any nucleotide except T. Thus, all of the 3' terminal cDNA restriction fragments including a poly A region are classified into 192 (=16×12) groups by 192 PCR reactions each separately. PCR was carried out with Ex Taq DNA polymerase (Takara, Japan) and cycling parameters were 30 s at 94° C., 1 min at 56° C., and 1 min at 72° C. (30 cycles). The amplified products were separated by polyacrylamide gel (4%T, 5%C) electrophoresis containing 1×TBE (0.09 M Tris-borate and 0.02 M EDTA) and 7 M Urea on a Hitachi SQ-3000 fluorescent DNA sequencer.

The cDNA's of interest were cut from the gel and purified by the crush and soak method. FIG. 2 shows a sample gel yielding six candidates. The bands represent a particular fragment that is more abundant in the lung cancer RNA than the normal blood. Bands were isolated if they were present in at least 2 of the 6 lung cancer tissue lanes and not in either normal blood lane. Because differential display frequently produces many false positives, the selection criterion was important. The isolated fragments were subcloned using pGEM-Teasy Vector Systems (Promega, USA). The products that were purified by mini-preparation were sequenced with T7 primer (5'-TAATACGACTCACTATAG-3') [SEQ ID NO:15] using Big Dye terminator cycle sequencing kit (Applied Biosystems, CA, USA) and an ABI Prism 377 DNA sequencing apparatus (Applied Biosystems).

Northern Blot Analysis

Total RNA was separately by formaldehyde gel electrophoresis and transformed to nylon membrane (+) (Amersham Pharmacia, England). Candidates were cloned with pCR2-1. Clones were verified by sequence analysis. Plasmid DNA was restricted with appropriate enzyme and used for in vitro transcription.

Selection Method

Initially, 121 candidates which were negative in healthy blood and positive in lung cancers were identified. After sequencing these 121 candidates, the sequences were analyzed for homology with known sequences in GenBank as well as Expressed Sequence Tag (EST) databases.

The procedure for the selection of real versus false signals was as follows: Bands of interest were excised form the display gel and the DNA was cloned. The isolates of interest were then sequenced. If the sequence data indicated that the gene was normally present in blood cells it was discarded. Then specific primers were designed and PCR was carried out for each clone. First, normal blood RNA was amplified by PCR and if a PCR product was produced, the candidate was discarded. The remaining 21 candidates were tested against blood from lung cancer patients, and if no signal was found in any patient, then the candidate was discarded. This procedure resulted in the isolation of 4 candidates (see Example 2).

TABLE 1

CANDIDATE MARKERS FOR LUNG CANCER BLOOD DETECTION

| Candidate | Database | Description |
| --- | --- | --- |
| Synd | nr | Syndecan-1 gene (exon 2-5) |
| Col | nr | Pro- 2(1)collagen COL1A2gene (exon 1) |
| 7013 | EST | Genomic clone Location 1q32.2 |
| 7018 | EST | none |

EXAMPLE 2

Candidate Genes

The candidate markers are shown in Table I. The first candidate marker found was identified as the syndecan 1 gene (nucleotide sequence PubMed accession number BC008765, protein sequence accession number AAH08765) (SEQ ID NOS:18 and 19). FIG. 6 provides the sequence of the fragment provided by s-AFLP (SEQ ID NO:22). A blast search of this sequence produced a match for exons 2–6 of the Syndecan 1 gene (genbank accession No. Z48199). Syndecan 1 is a cell surface transmembrane heparan sulfate proteoglycan from the family of proteoglycans that binds to extracellular matrix and growth factors. Loss of regulation of this gene has been identified in several cancers.

The next candidate was identified as collagen 1 alpha 2 (nucleotide sequence PubMed accession number J00114, protein sequence accession number AAA51996) (SEQ ID NOS:20 and 21). FIG. 7 provides the sequence of the old fragment provided by s-AFLP(SEQ ID NO:24) as well as the new fragment (SEQ ID NO:23). A blast search of this sequence provided a match for exon 1 of the collagen pro-alpha2(I) gene (genbank accession No. J03464). This is a widely expressed gene, especially in lung. It is interesting that the gene is involved as a fusion protein with PLAG1 (pleomorphic adenoma gene 1) in lipoblastoma.

The third candidate was termed 7013 (SEQ ID NO:16) and was identified as a novel gene when searched against EST databases. FIG. 8 provides the sequence of the fragment obtained from s-AFLP (SEQ ID NO:25). This fragment was used to identify a larger fragment using primer extension (SEQ ID NO: 16). This larger fragment was cloned into pCRII and the resulting plasmid p7013 has been deposited under the Budapest Treaty with the ATCC in Bethesda, Md., USA on Jun. 21, 2001 by FEDEX shipment with label No. 822080437778 and assigned ATCC accession No. PTA-3471. A larger clone was isolated from a cDNA library, and the plasmid p7013/12 has been deposited with the Budapest Treaty with the ATCC in Bethesda, Md., USA on Jun. 21, 2001 by FEDEX shipment with label No.822080437778 and assigned ATCC accession No. PTA-3473. The plasmid has an insert of approximately 2200 bases in pCMV6-XL4. Upon doing a BLAST search an EST (Genbank Accession number AK002208) was identified which showed the highest, homology and a genomic clone (Genbank Accession number AL035408). The sequence does not exhibit any homology with any known gene, but has been localized to chromosome I region q32, a region which has been reported to undergo amplification in several epithelial cancers.

The next candidate was termed 7018 (SEQ ID NO: 17) and is also a novel gene. FIG. 9 provides the sequence of the fragment obtained from s-AFLP (SEQ ID NO:26). This sequence was used to primer extend into the cDNA to get a larger fragment (SEQ ID NO: 17). This larger fragment was cloned in plasmid pCRII and and the resulting plasmid p7018 has been deposited with the Budapest Treaty with the ATCC in Bethesda, Md., USA on Jun. 21, 2001 by FEDEX shipment with label No.822080437778 and assigned ATCC accession No. PTA-3472. Upon doing a BLAST search two ESTs (Genbank Accession numbers AW956727 and AW452795) were identified which showed the highest homology, but does not exhibit any homology to known genes. In addition, it is not localized to anychromosomal region as of yet.

These deposits were made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited strain is not to be construed as a license to practice the invention in contravention of the rights granted under the authority of any government in accordance with its patent laws.

Examples 3 and 4 identify whether the markers are expressed by normal lung cells and lung cancer cell lines.

EXAMPLE 3

Expression of the Markers in Normal Lung Cells and Lung Cell Lines

To identify whether these markers were expressed in normal human lung cells, RT-PCR was performed on normal human lung RNA using identical amount of RNA from human lung small airway epithelial cells, micro-vascular endothelial cells from the lung, bronchial epithelial cells and normal human lung fibroblasts.

Total RNA Preparation from Normal Lung or Lung Cancer Cell Lines

Total RNA from cells was isolated by the acid-guanidine thiocyanate/phenol/chloroform extraction using the TRI REAGENT® protocol (Molecular Research Center, Inc., Cincinnati, Ohio, USA). It is not necessary for the RNA to be purified completely, in fact, some DNA contamination is acceptable if the primer is designed at an intron-spanning region.

RT-PCR

Before reverse transcription, all of the RNA samples were treated with DNase I to ensure that there was no genomic DNA contamination. One unit of DNase I (Life Technologies) was used for every one μg of total RNA. The products were extracted with phenol/chloroform twice and ethanol precipitated. The cDNA was synthesized with 200 units of MMLV transcriptase for each 0.5 μg of RNA (42° C. for 50 min.) from cell lines and with 100 units of transcriptase ReverTraAce™ for each one μg from blood total RNA (37° C. for 60 min.).

First, cDNA synthesis was performed with 100 units of reverse transcriptase ReverTraAce™ (TOYOBO, Japan) for each one μg of total RNA, 50 μg/ml of oligo(dT)$_{12-18}$ primer (Life Technologies), 500 μM of each deoxynucleotide triphosphate (dNTP) (Life Technologies) for 60 min at 37° C. For every PCR, 50 ng of total RNA, 10 pmol of primer pairs and 0.125 units of EX Taq DNA polymerase was used in a total volume of 25 μl reaction. Primer pairs and cycling conditions for each genetic marker were as follows: SYND marker was amplified with primer rP5 (5'-TCATGTGTG-CAACAGGGTAT-3') [SEQ ID NO:5] and primer P6 (5'-AATATTCCTGATTCCAGCCC-3')[SEQ ID NO:6]. Cycling conditions were 30 sec at 94° C., 1 min at 65° C., and 1 min at 72° C. (30 cycles). COL was amplified with primer P7 (5'OAGAGCATTGTGCAATACAGTTTCAT-TAACTCCT-3')[SEQ ID NO:7] and primer P8 (5'-GGTTTTCTTACAAAGGTTGACATTTTCCTAACAG-3') [SEQ ID NO:8]. Cycling parameters were 30 sec at 94° C., 1 min at 58° C., and 1 min at 72° C. (20 cycles). For the second round of the PCR reaction, the reaction mix contained 1 μl of the first round PCR product as a template and the primer pair P3 and P4. The second step of PCR was cycled at 94° C. for 30 s, at 60° C. for 1 min and 72° C. for 1 min for 20 rounds. 7013 was amplified with primer P9 (5'-AATGAAGGAGACATCTGGAGTGTGCG-3')[SEQ ID NO:9] and primer P10 (5'-AGAAAAGAAAGATTAAGGT-TCCCATCTGCG-3')[SEQ ID NO:10]. Cycling conditions were 30 sec. at 94° C., 1 min at 63° C., and 1 min at 72° C. (38 cycles). 7018 was amplified with primer P11 (5'-ATC-CATGCACGTCACTTTCCTTTCC-3')[SEQ ID NO:11] and prime P12 (5'-TCAAGTAGGCACAACCCAGTCCT-3')[SEQ ID NO:12]. Cycling conditions were 30 sec at 94° C., 1 min at 63° C., and 1 min at 72° C. (38 cycles). CK-19 was amplified with primer P13 (5'-CAAGATCCTGAGT-GACATGCGAAG-3')[SEQ ID NO:13] and primer P14 (5'-CGCTGATCAGCGCCTGGATATG-3')[SEQ ID NO:14]. Cycling parameters were 30 sec at 94° C., 1 min at 60° C. and 1 min at 72° C. (20 cycles). For the second PCR reaction, one μl of the first round PCR product was a template and same primer pairs of P13 and P14 with identical cycle parameter. Following PCR, one μl of PCR products was analyzed by electrophoresis on a 4% NuSieve GTG agarose gel (Takara, Japan).

As positive controls, all samples were subjected to PCR for μ-actin. Primers for four candidates, 7018, 7013, Syndecan 1 (Synd), Collagen 1A2 (Col), and a positive control, Cytokeratin-19 (Ck-19) were used for RT-PCR.

Cytokeratin-19 is well known as an epithelial cell marker. PCR amplifications were performed with the use of the five primer pairs for these markers. For cell lines, 0.1 volume of RT reaction, 10 μM of each primer and 1.24 units of Taq DNA polymerase were used in a total volume of 50 μl reaction. For whole blood, 0.1 volume of RT reaction, 10 μm of each primer and 0.125 units of EXTaq DNA polymerase were used in total volume of 25 μl reaction. The PCR conditions of each primers as shown in Table 2. PCR products were analyzed by agarose gel electrophoresis and some products were confirmed by sequencing.

TABLE 2

PCR conditions for each primer pair

| marker | initial denaturation | PCR cycle | | | final extension |
| --- | --- | --- | --- | --- | --- |
| | | denaturation | annealing | extension | |
| 7018 | 94° C. for 1 min. | (94° C. for 30 sec. | 53° C. for 30 sec. | 72° C. for 1 min) × 35 | 72° C. for 5 min. |
| 7913 | 94° C. for 1 min. | (94° C. for 30 sec. | 60° C. for 30 sec. | 72° C. for 1 min) × 35 | 72° C. for 5 min. |
| Synd | 94° C. for 1 min. | (94° C. for 30 sec. | 55° C. for 30 sec. | 72° C. for 1 min) × 35 | 72° C. for 5 min. |
| Col | 94° C. for 1 min. | (94° C. for 30 sec. | 52° C. for 30 sec. | 72° C. for 1 min) × 35 | 72° C. for 5 min. |
| Ck-19 | 94° C. for 1 min. | (94° C. for 30 sec. | 65° C. for 30 sec. | 72° C. for 1 min) × 35 | 72° C. for 5 min. |
| β-actin | 94° C. for 1 min. | (94° C. for 30 sec. | 53° C. for 30 sec. | 72° C. for 1 min) × 35 | 72° C. for 5 min. |

Figure 3:
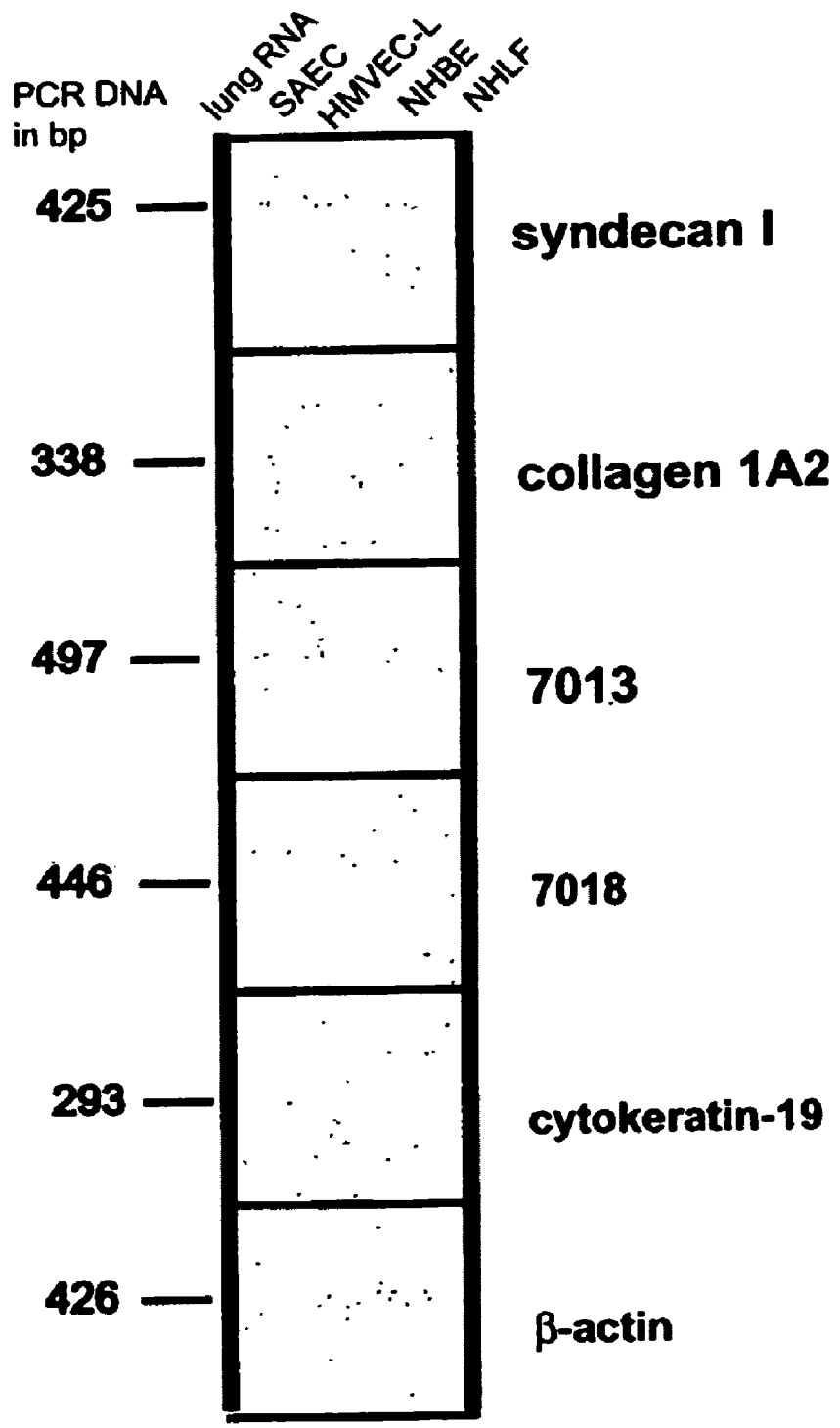
FIG. 3 is a gel showing RT-PCR of lung cells with each candidate marker as well as cytokeratin-19 and -actin.

The results of the PCR of normal cells is shown in Table 3. This shows that the four newly isolated markers were frequently expressed in normal lung cell lines examined. In addition, the new markers, 7013 and 7018 are specific for lung epithelial cells (Table 3 and see also, FIG. 3). The syndecan I was found to be expressed in all five RNA's. The collagen gene was also expressed in all five. The 7013 gene was found only in total lung cancer tissue and the epithelial cells as was 7018. The marker for lung cancer cytokeratin-19 was also found only in total lung and epithelial cells.

TABLE 3

RT-PCR amplification of mRNA markers in lung RNA and lung cell line RNA

| | 7018 | 7013 | Synd | Col | Ck-19 |
| --- | --- | --- | --- | --- | --- |
| Total lung RNA | + | + | + | + | + |
| SAEC (small airway epithelial cell) | + | + | + | + | + |

TABLE 3-continued

RT-PCR amplification of mRNA markers in lung RNA and lung cell line RNA

|  | 7018 | 7013 | Synd | Col | Ck-19 |
|---|---|---|---|---|---|
| NHBE (bronchial epithelial cell) | − | + | + | + | + |
| HMVEC-L (micro-vascular endothelial cell in lung) | − | − | + | + | − |
| NHLF (lung fibroblast) | − | − | + | + | − |

EXAMPLE 4

Expression of the Markers in Lung Cancer Cell Lines

To identify whether these markers were expressed in lung cancer cell lines, RT-PCR was performed on RNA from 12 lung cancer cell lines using identical amounts of RNA (see Table 4). All PCR products were analyzed by agarose gel electrophoresis and some products were confirmed by sequencing. All RNA's amplified the positive control actin equally well. Cancer cell lines Lu99 (Yamada, et al. Giant cell carcinomas of the lung producing colony-stimulating factor in vitro and in vivo. Jpn. J. Cancer Res., 76:967–976, 1985), PC13 (large cell carcinoma), A549 (Imanishi, et al. Inhibition of growth of human lung adenocarcinoma cell lines by anti-transforming growth factor-alpha monoclonal antibody. J. Natl. Cancer Inst., 81:220–23, 1989), PC14, NC1-H441 (adenocarcinoma), PC1, and QG56 (squamous cell carcinoma) were used.

Figure 4:
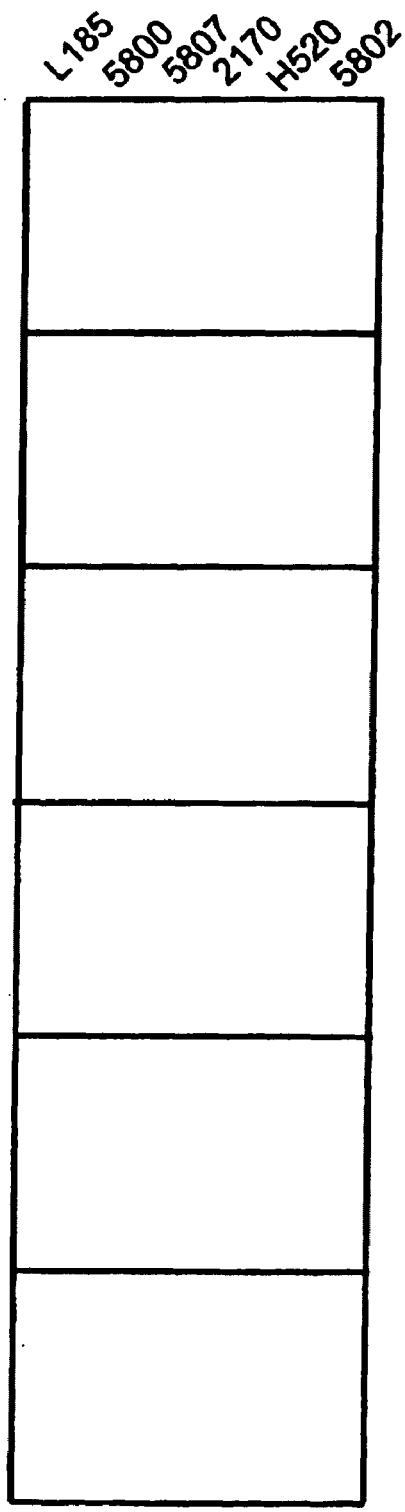
FIG. 4 is a gel showing RT-PCR of lung cancer cells with each candidate marker as well as cytokeratin-19 and -actin.

The presence of the markers in the RNA in 6 lung cancer cell lines was also examined by RT-PCR as shown in FIG. 4. Four of the lines were adenocarcinomas and the ones in lanes 5 and 6 were squamous carcinoma. Syndecan 1 was found expressed in all six. The collagen gene was found strongly in four and weakly in two of the six. Interestingly 7013 and 7018 displayed different expression patterns. 7013 was found in four of six and 7018 in five of six lines. This is compared to the cytokeratin-19 which was found in five of six. The squamous line 5082 did not express cytokeratin-19, but did express 7018.

TABLE 4

RT-PCR expression markers from lung cancer cell lines

| cell line | cell type | 7018 | 7013 | Synd | Col | Ck-19 |
|---|---|---|---|---|---|---|
| A549 | adenocarcinoma | + | + | + | + | + |
| PC14 | adenocarcinoma | − | + | − | − | − |
| NCI-H23 | adenocarcinoma | − | + | + | + | + |
| NCI-H358 | adenocarcinoma | + | + | + | + | + |
| NCI-H441 | adenocarcinoma | + | + | + | − | − |
| SW 1573 | adenocarcinoma | + | − | + | + | + |
| QG 56 | squamous cell | + | + | + | + | + |
| PC 1 | squamous cell | + | + | − | + | − |
| NCI-H157 | squamous cell | + | − | + | + | − |
| NCI-H520 | squamous cell | + | + | + | + | + |
| Lu 99 | large cell | − | − | − | − | + |
| Pc 13 | large cell | + | + | − | − | − |

Example 5 provides a method for the identification of lung cancer cells in blood using these markers. In Example 5, RT-PCR is used to identify the presence of mRNA for these markers in a blood sample.

EXAMPLE 5

Expression of the Markers in Patient Blood 68 patients with lung cancer who were diagnosed and treated at Keio University Hospital between November 1998 and April 2000 were studied as well as 7 patients with metastatic lung cancer at Keio University Hospital in the same period. The characteristics of the patients are shown in Table 5.

The RNA from patient blood samples was tested using RT-PCR with the four candidates, 7018, 7013, Syndecan 1 (synd), Collagen 1A2 (Col), and a positive control, Cytokeratin-19 (Ck-19). In order to qualify as a positive result, the sample had to have a successful amplification of the marker as well as a successful amplification of the -actin.

Total RNA Preparation from Whole Blood

Peripheral blood samples were taken from the antecubital vein of patients and healthy volunteers in heparin anticoagulant containing tubes. Red blood cells (RBCs) were lysed by standard hypotonic solutions, and the whole blood cell population was collected onto a RiboCap syringe filter (RNAture, Irvine, Calif.). RNA was eluted from the syringe filter by applying a guanidine solution followed by a standard AGPC method. Purified total RNA qualities were analyzed by agarose gel electrophoresis with 18s and 28s ribosomal RNA bands and their quantity were measured by UV spectrometer. After preparation, the RNA pellet was resuspended in 20 µl of diethylpyrocarbonate (DEPC)-treated water and store at −80° C.

RT-PCR

Before reverse transcription, all RNA samples were treated with DNase I to remove any possible genomic DNA contamination. The cDNA was synthesized with 200 units of MMLV transcriptase for each 0.5 µg of RNA (42° C. for 50 min.) from cell lines and with 100 units of transcriptase ReverTraAce™ for each one µg from total blood RNA (37° C. for 60 min.).

All samples were subjected to PCR for β-actin as a positive control. FIG. 5 gives an example of a positive test from blood RNA. Primers for the four candidates, 7018, 7013, Syndecan 1 (synd), Collagen 1A2 (Col), as well as Cytokeratin-19 (Ck-19) which is well known as an epithelial cell marker were used for RT-PCR. For RT-PCR of cell lines: 0.1 volume of RT reaction, 10 µM of each primer and 1.24 units of Taq DNA polymerase were used in a total volume of 50 µl reaction. For RT-PCR of whole blood: 0.1 volume of RT reaction, 10 µm of each primer and 0.125 units of EXTaq DNA polymers were used in total volume of 25 µl reaction. The PCR conditions were as in Table 2.

TABLE 5

Characteristics of Lung Cancer Patients

| Group | Characteristic | Number |
|---|---|---|
| Gender | Male | 48 |
|  | Female | 20 |
| Age | –39 | 1 |
|  | 40–49 | 14 |
|  | 50–59 | 8 |
|  | 60–69 | 18 |
|  | 70–79 | 25 |
|  | 80– | 2 |

TABLE 5-continued

Characteristics of Lung Cancer Patients

| Group | Characteristic | Number |
|---|---|---|
| Stage | IA | 9 |
|  | IB | 6 |
|  | IIA | 0 |
|  | IIB | 2 |
|  | IIIA | 12 |
|  | IIIB | 15 |
|  | IV | 15 |
|  | Recurrence | 8 |
|  | Unknown | 1 |
| Histology | Adenocarcinoma | 35 |
|  | Squamous Cell Carcinoma | 19 |
|  | Large Cell Carcinoma | 3 |
|  | Small Cell Carcinoma | 2 |
|  | Adenosquamous Cell Carcinoma | 1 |
|  | Unknown | 8 |

In Table 6, the results of RT-PCR of the blood from lung cancer patients and control healthy volunteers was tested for the presence of the identified markers. Stage I–IV patients were tested for expression of the markers as were 40 healthy volunteers. In summary, the results showed that the four genes; 7018, 7013, Synd and cal were not expressed in the healthy control bloods, but were in cancer cell lines (see Table 6).

TABLE 6

Results of RT-PCR Analysis in Lung Tumor Patients

| Patients | N | Synd | Col | 7013 | 7018 | % |
|---|---|---|---|---|---|---|
| Stage I–IV | 68 | 13 | 9 | 25 | 3 | 54 |
| Healthy | 20 | 0 | 0 | 0 | 1 | 5 |

More specifically, In Table 7, in lung cancer patients' blood samples, each gene was expressed 3%, 41%, 19%, and 16% respectively, but at least one of these four genes is expressed in 57% of patient's blood samples. Also, using cytokeratin-19, at least one of these five genes is expressed in 71% of patients. One or more of these genes are expressed in 80.5% of adneocarcinoma and in 68.4% of squamous cell carcinoma.

Syndecan was found in 13 lung cancer patients and no control (healthy) patients. Collagen was only found in lung cancer patients. The 7013 marker was widely expressed in lung cancer patients and not a single control. Only 7018 was found to be expressed in a control sample as well as the lung cancer patients.

TABLE 7

Frequency of positive RT-PCR expression markers in lung cancer patients' blood

| Cell type | No. of Pt. | 7018 | 7013 | Synd | Col | combination of 4 | Ck-19 | combination of 5 |
|---|---|---|---|---|---|---|---|---|
| Adeno | 34 | 2 | 14 | 8 | 5 | 22 | 10 | 27 |
| Squamous | 21 | 1 | 7 | 3 | 2 | 10 | 7 | 13 |
| Large | 3 | 0 | 1 | 1 | 0 | 2 | 0 | 2 |
| Adenosq. | 1 | 0 | 0 | 0 | 0 | 0 | 0 | 0 |
| Small | 2 | 0 | 1 | 0 | 1 | 1 | 1 | 1 |
| Unknown | 8 | 0 | 3 | 1 | 1 | 4 | 3 | 6 |
| Total | 69 | 3 | 26 | 13 | 9 | 39 | 21 | 49 |

Therefore, 54% of the patients displayed at least one or more of the four markers.

In summary, four new potential markers have been identified which are present in lung cancer patient's blood and absent from normal blood. Two of the markers are novel genes.

The new markers in combination were observed in 54% of lung cancer patients' blood examined (Table 5) and combining these markers with cytokeratin-19 resulted in the markers being found in 68% of lung cancer patients' blood examined. Therefore, the combination would be ideal for the diagnosis of micrometastasis of lung cancer in the early stage or for relapse.

In example 6, the ability of the assay using the 5 markers to identify a lung cancer cell in any type or stage of lung cancer is explored.

EXAMPLE 6

Analysis by Type and Stage of Lung Cancer

Patients with different types and stages of lung cancer were tested for expression of the four makers (see Table 8).

TABLE 8

Characteristics of metastatic lung cancer patients.

| Origin (Cell type) | Age | Gender |
|---|---|---|
| Bile duct (adenocarcinoma) | 59 | F |
| Colon (adenocarcinoma) | 60 | F |
| Breast (adenocarcinoma) | 68 | F |
| Uterus (squamous cell carcinoma) | 68 | F |
| Uterus (squamous cell carcinoma) | 55 | F |
| Esophagus (squamous cell carcinoma) | 56 | M |
| Larynx (squamous cell carcinoma) | 59 | M |

As in Example 5, Sixty-nine lung cancer patient blood samples were obtained from Keio University Hospital. The staging classification was performed according to tumor-node-metastasis (TNM) score (Mountain CE: A new international staging system for lung cancer. Chest 89:225S–233S, 1986). The RNA was purified and RT-PCR performed as in Example 5. Expression of each marker in the blood samples was analyzed and the results are shown in Table 9.

In Table 9, it can be seen that although the markers were somewhat more likely to be expressed in later stages, if the combination of all 5 is used, they can be identified in all stages of the disease. Thus, using these five genes in combination, at least one gene is expressed in 56% of stage IA, 33% in IB, 50% in II, 921 in IIIA, 60% in IIIB and 87% in IV.

TABLE 9

Frequency of positive RT-PCR expression markers in lung cancer patients' blood by stage

| Stage | 7018 | 7013 | Synd | Col | Combination of 4* | Ck-19 | Combination of 5** |
|-------|------|------|------|-----|-------------------|-------|---------------------|
| IA    | 1    | 2    | 0    | 3   | 4 (44%)           | 2     | 5 (56%)             |
| IB    | 0    | 1    | 1    | 1   | 2 (33%)           | 1     | 3 (50%)             |
| II    | 0    | 0    | 1    | 0   | 1 (50%)           | 1     | 2 (100%)            |
| IIIA  | 0    | 9    | 4    | 0   | 10 (83%)          | 2     | 11 (92%)            |
| IIIB  | 2    | 2    | 3    | 3   | 7 (44%)           | 5     | 9 (56%)             |
| IV    | 0    | 9    | 3    | 2   | 11 (69%)          | 8     | 13 (81%)            |
| Rec.  | 0    | 3    | 1    | 0   | 4 (50%)           | 2     | 6 (75%)             |

*combination of 4 markers: 7013, 7018, Synd, and Col
**combination of 5 markers: 7013, 7018, Synd, Col, and Ck-19

When blood from patients with metastatic disease was tested, it can be seen that at least one marker was detected in all types of metastatic disease (see Table 10). This suggests that the markers can be used to detect disease in all stages of lung cancer as well as detecting recurrent metastases.

TABLE 10

Marker detection in metastatic lung cancer patient's blood

| Origin (cell type) | 7018 | 7013 | Synd | Col | Ck-19 |
|--------------------|------|------|------|-----|-------|
| Bile duct (adeno)  | −    | +    | −    | −   | −     |
| Colon (adeno)      | +    | −    | +    | +   | −     |
| Breast (adeno)     | +    | +    | −    | −   | +     |
| Uterus (squamous)  | −    | −    | −    | −   | −     |
| Uterus (squamous)  | −    | −    | −    | +   | +     |
| Esophagus (squamous)| −   | +    | +    | −   | +     |
| Larynx (squamous)  | −    | +    | −    | −   | −     |

EXAMPLE 11

Diagnosis and Analysis of the Presence of Lung Cancer Using mRNA from one or More of the Identified Markers The blood from a patient is isolated and the RNA from the blood sample purified. RT-PCR is performed using at least one of the following markers: syndecan 1, collagen 1 alpha 2, 7013, and 7018. Controls such as -actin are also performed. Alternatively, the additional marker cytokeratin-19 is also tested by RT-PCR. The results are pooled and analyzed for expression of each marker.

EXAMPLE 12

Diagnosis and Analysis of the Presence of Lung Cancer Using Antibodies to one or More of the Identified Markers Monoclonal or polyclonal antibodies specific for the markers: syndecan 1, collagen 1 alpha 2, 7013, and 7018, and cytokeratin-19 are purchased, prepared, or isolated from patient blood. The antibodies are prepared using methods known to one of skill in the art, including hybridoma technology, injection of a fusion protein into rabbits, production of humanized antibodies, library technology, etc. In addition, whole antibodies or functional parts may be used. The blood from a patient is isolated and the cells treated with antibodies to one or more of the identified markers. The antibodies are fluorescently labeled or alternatively, the secondary antibodies are fluorescently labeled. Cells bearing these markers are identified by the presence of the fluorescent label using FACS technology. Each marker is identified using a different fluorescently labelled antibody, allowing the identification of more then one marker in a single blood sample.

EXAMPLE 13

Isolation of Cancer Cells from Blood or Bone Marrow

The metastatic cancer cells are isolated from the blood or bone marrow by treating the cells or a non-lung tissue containing the cells with antibodies specific for at least one marker selected from the group consisting of: syndecan 1, collagen 1 alpha 2, 7013, and 7018 and cytokeratin-18.

The antibodies are bound to a moiety selected from the group consisting of: metallic particles, fluorescent particles, chromatography beads, a chromatography gel and a solid support.

The isolated cells can then be used for identification of the site from which the cancer cells metastasized or production of activated immune cells specific for the cancer. Alternatively, the method can be used to purify the cells from the blood.

EXAMPLE 14

Isolation of a Full-Length cDNA Clone

The clone obtained from the s-AFLP technique is used to design primers for detection of a full-length cDNA clone. A human cDNA library is purchased from Stratagene (Torrey Pines, Calif.). The library is screened using a probe specific to 7013 (SEQ ID NO:16) or 7018 (SEQ ID NO:17). After obtaining positive clones, the clones are tested using PCR and sequenced.

EXAMPLE 15

Identification of a Cellular Epithelial Origin/Carcinoma

Because the markers 7013 and 7018 specifically identified cells with an epithelial origin. The markers are used to identify whether cells have an epithelial origin, or in the case of cancer, whether it is a carcinoma. The cells are treated as in Example 12 for FACS analysis, using only the markers 7013 and 7018. If the cells are fluorescently labelled by one or both markers, the cell is determined to be of epithelial origin, or a carcinoma.

What is claimed is:

1. An isolated or purified polynucleotide consisting of SEQ ID NO: 16.

2. An isolated or purified polynucleotide fragment of SEQ ID NO: 16 consisting of at least 17 consecutive nucleotides of SEQ ID NO: 16 or the complement thereof.

3. A method for the identification of lung cancer in a human patient comprising:
   isolating blood from a human patient,
   identifying the presence of a polynucleotide consisting of SEQ ID NO: 16 wherein the presence of SEQ ID NO: 16 is indicative of lung cancer.

4. The method of claim 1, further comprising identifying the presence of the marker cytokeratin-19.

5. The method of claim 1, wherein at least two markers are identified.

6. The method of claim 4, wherein more than two markers are identified.

7. The method of claim 1 wherein said identification is by RT-PCR.

8. A method for the identification of metastases of a lung tumor in a human patient comprising:
   isolating blood from a human patient,
   identifying the presence of a polynucleotide consisting of SEQ ID NO: 16 wherein the presence of SEQ ID NO: 16 is indicative of metastases of lung cancer.

9. The method of claim 8, wherein said metastases of a solid tumor is selected from the group consisting of bile duct, colon, breast, uterus, esophagus, and larynx.

10. A plasmid p7013, having ATCC accession number PTA-3471.

11. A plasmid p7013/12, having ATCC accession number PTA-3473.

* * * * *